United States Patent [19]
Cherry et al.

[11] 4,290,949
[45] Sep. 22, 1981

[54] ESTERS OF 2-VINYLCLAV-2-EM-3-CARBOXYLIC ACID AND PROCESS FOR PREPARING SAME

[75] Inventors: Peter C. Cherry, South Harrow; Christopher E. Newall, Ealing; Nigel S. Watson, Greenford; Gordon I. Gregory, Chalfont St. Peter; Peter Ward, Northolt, all of England

[73] Assignee: Glaxo Operations UK Limited, Greenford, England

[21] Appl. No.: 809,915

[22] Filed: Jun. 24, 1977

[30] Foreign Application Priority Data

Jun. 25, 1976 [GB] United Kingdom ............... 26595/76
Sep. 9, 1976 [GB] United Kingdom ............... 37446/76

[51] Int. Cl.³ .......................................... C07D 498/04
[52] U.S. Cl. ................................................ 260/245.3
[58] Field of Search ........... 260/307 F, 307 FA, 245.3

[56] References Cited

FOREIGN PATENT DOCUMENTS

849308 12/1976 Belgium .
5901 of 1976 South Africa .

*Primary Examiner*—Mark L. Berch
*Attorney, Agent, or Firm*—Bacon & Thomas

[57] ABSTRACT

2-Vinylclavem compounds are disclosed which have been found of value in the synthesis of thio-derivatives of clavulanic acid which possess antibiotic and β-lactamase inhibitory activity. Methods for preparing the vinylclavem compounds are disclosed and processes for preparing the thio-derivatives are given.

1 Claim, No Drawings

ESTERS OF 2-VINYLCLAV-2-EM-3-CARBOXYLIC ACID AND PROCESS FOR PREPARING SAME

This invention relates to new antibiotic intermediates and to a process for their production.

In our German OLS No. 2,604,697, we have described the isolation, from fermentations of *Streptomyces clavuligerus*, of the carboxylic acid having the formula (I) (clavulanic acid) and salts thereof in pure form.

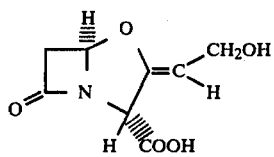

The bicyclic compounds in this specification are named with reference to "clavam"; the name being given to the parent heterocycle of formula A

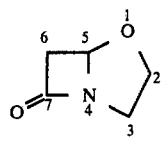

by analogy with the term "cepham" used in the naming of cephalosporin compounds in J. Amer. Chem. Soc. 1962, 84, 3400. Thus, the compound of formula (I) is named (3R,5R,Z)-2-(2-hydroxyethylidene)-clavam-3-carboxylic acid.

We have now been able to prepare diene compounds related to the compound of formula (I) above and according to one aspect of the invention, we provide compounds of the formula (II)

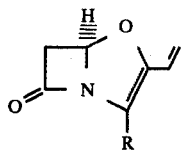

wherein R represents an esterified carboxyl group.

The carboxylic acid esters according to the invention may in general be represented as compounds of formula (II) in which R is a group $COOR^1$ where $R^1$ represents an organic group which is conveniently derived from an alcohol (aliphatic or araliphatic), a phenol, or a stannanol. Such an alcohol, phenol or stannanol used to esterify the carboxyl group preferably contains not more than 24 carbon atoms.

Thus, the group $R^1$ may represent a straight or branched unsubstituted or substituted alkyl or alkenyl group preferably having from 1–8 carbon atoms, for example a methyl, ethyl, propyl or isopropyl, butyl, sec-butyl, tert-butyl or allyl group, desirable substituents being for example, alkoxy e.g. methoxy; halogen, i.e. fluorine, chlorine, bromine or iodine; cyano; acyloxy, e.g. alkanoyloxy such as acetoxy or pivaloyloxy or alkoxycarbonyloxy e.g. ethoxycarbonyloxy; acyl e.g. p-bromobenzoyl and alkoxycarbonyl e.g. ethoxycarbonyl;

an aralkyl group having up to 20 carbon atoms especially an arylmethyl group e.g. a benzyl or substituted benzyl group, suitable substituents being either halo e.g. chloro; nitro e.g. o-nitro or p-nitro; cyano; alkoxy e.g. p-methoxy or alkyl e.g. p-methyl groups; a diphenylmethyl or triphenylmethyl group or a fur-2-ylmethyl, thien-2-ylmethyl or pyrid-4-ylmethyl group, the heterocyclic groups of which may also be substituted e.g. by a $C_{1-4}$ alkyl group, preferably methyl;

an aryl group having up to 12 carbon atoms, e.g. a phenyl or substituted phenyl group, suitable substituents being either halo e.g. chloro; nitro e.g. o- or p-nitro; cyano; alkoxy e.g. p-methoxy or alkyl e.g. p-methyl groups;

a cycloalkyl group containing not more than 12 carbon atoms, e.g. adamantyl;

a heterocyclic group containing not more than 12 carbon atoms, the heteroatom being, for example, oxygen as in the tetrahydropyranyl or phthalidyl group, or a stannyl group having up to 24 carbon atoms for example a stannyl group carrying three substituents, which may be the same or different, selected from alkyl, alkenyl, aryl, aralkyl, cycloalkyl, alkoxy, aryloxy or aralkoxy groups. Such groups will include methyl, ethyl, propyl, n-butyl, phenyl and benzyl groups.

The compounds of the invention are important as intermediates for the synthesis of other derivatives of the compound of formula (I). They have, for example, been found to undergo facile 1,4-addition of sulphur nucleophiles in the presence of a substantially non-nucleophilic base e.g. a tertiary amine, to provide antibiotic derivatives of the compound of formula (I) wherein the hydroxyl group of the hydroxyethylidene group is replaced by the residue of a sulphur nucleophile, e.g. a thio- group; such compounds and their preparation are described in greater detail hereinafter.

Where the diene of formula II is to be used to prepare a derivative such as one of the above thio-analogues, which is to be used in the form of the free acid or a salt thereof, the group $COOR^1$ in the diene is preferably one which is readily cleaved to carboxyl, e.g. by hydrogenolysis, for example a benzyl, p-nitrobenzyl, benzhydryl or trityl group. Where the ultimate product is to be an ester, however, it may be convenient for the diene ester to carry the same ester group as is required in the final product, for example an alkyl ester; e.g. methyl ester group.

According to another aspect of the invention we provide a process for the preparation of the diene compounds of formula (II) wherein a compound of the formula (III)

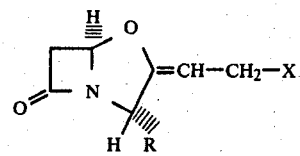

(wherein R is as defined above and X is a readily eliminatable substituent) is treated with a substantially non-nucleophilic base, whereby a compound of formula (II) is obtained.

The compound of formula (III) may be in the form either of its E- or Z-isomer or mixtures thereof.

The term "substantially non-nucleophilic base" as used herein is intended to mean bases which will function as bases without significant nucleophilic attack on the β-lactam reactant or product during the reaction. The diene of formula (II) is sensitive to nucleophilic attack, as are the other clavams referred to herein; since most bases are capable of acting as nucleophiles to some extent, depending on the time for which they are allowed to react, the reactants and products preferably should not be allowed to stand in the presence of a base after the principal reaction is complete, in order to avoid side reactions.

The base will desirably be a tertiary organic base, e.g. a tertiary amine. Suitable amines will include amines bearing aliphatic, araliphatic or aromatic groups, e.g. alkyl groups having up to 8 carbon atoms, aralkyl groups having up to 6 carbon atoms in the alkyl portion, or an aryl group, such aryl and aralkyl groups desirably being monocyclic. Amines bearing cycloaliphatic e.g. $C_{3-7}$ cycloalkyl groups or amines wherein the nitrogen atom forms part of a five-, six- or seven-membered heterocyclic ring optionally containing a further heteroatom, e.g. N-alkyl piperidines or N-alkyl morpholines, are also suitable.

Preferred bases include trialkylamines preferably having 1-6 carbon atoms in each alkyl group, especially methyl, ethyl, propyl or butyl groups, and triethylamine is particularly suitable.

Reaction will generally be effected in a suitable inert solvent. Such solvents will preferably have some degree of polarity and include esters e.g. ethyl acetate, ethers e.g. tetrahydrofuran, ketones e.g. acetone, amides e.g. dimethylformamide or halogenated hydrocarbons e.g. dichloromethane or 1,2-dichloroethane.

Reaction may be effected at low temperature, a temperature in the range $-30°$ C. to $+10°$ C., e.g. about $0°$ C. being preferred.

The substituent X may for example, be a halogen atom (chlorine, bromine or iodine) or an acyloxy group, such as an aliphatic, aromatic or araliphatic carbonyloxy or sulphonyloxy group, containing for example 1-20 carbon atoms. The aliphatic or aromatic grouping of such a sulphonyloxy group may for example be an alkyl (e.g. $C_{1-8}$) group, which may be substituted by a halogen atom e.g. fluorine or chlorine, or an aryl (e.g. $C_{6-15}$) group which may carry alkyl, e.g. methyl, alkoxy e.g. methoxy or halogen e.g. bromine substituents. The aliphatic or aromatic grouping of such a carbonyloxy group may be, for example, an alkyl (e.g. $C_{1-8}$) optionally substituted by one or more halogen atoms, e.g. chlorine or fluorine, or an aryl (e.g. $C_{6-15}$) group, optionally substituted by for example, one or more halogen atoms or nitro groups. Such acyloxy groupings may thus include dichloroacetoxy, mesyloxy, fluoromethanesulphonyloxy, tosyloxy or phenylsulphonyloxy.

Preferred substituents X are a chlorine or bromine atom or a mesyloxy group.

The compounds of formula (III) wherein X is a halogen atom may be prepared from esters of the compound of formula (I) by reaction thereof with a halogenating agent for example a compound of the formula XAY, where A is selected from SO, POX and PX, and X and Y are chlorine or bromine, or A is $SO_2$, X is chlorine or bromine, and Y is an alkyl or aryl group, the reaction in the latter case being carried out in the presence of halide ions. In a preferred method the halogenating agent will be phosphorus trichloride or phosphorus tribromide; or thionyl chloride or bromide. Thionyl chloride or bromide is preferred.

The ester compounds of formula (III) wherein X is a hydrocarbon sulphonyloxy group may readily be prepared by reaction of an ester of the compound of formula (I) with a sulphonylating agent. Sulphonylating agents include mesylating and tosylating agents, mesyl chloride being preferred.

The above reactions are generally effected in the presence of an acid binding agent such as pyridine.

The ester starting materials of formula (III) in which X is a carbonyloxy group may readily be prepared by reaction of an ester of the compound of formula (I) with an appropriate acylating agent, e.g. a carboxylic acid halide or anhydride.

In general, these reactions for the introduction of X may be carried out at temperatures in the range $-80°$ to $+20°$ C., preferably $-60°$ to $0°$ C. The solvents used in these reactions may be of the types described above in relation to the elimination of X. It is therefore possible and particularly convenient to carry out the reaction in the presence of the base serving to eliminate X, the diene of formula (II) being formed extremely rapidly.

As indicated above, reaction of an ester of the compound of formula (I) with a reagent capable of replacing hydroxyl by a readily eliminatable substituent X (as shown in formula (III)) in the presence of a suitable base yields the diene of formula (II) directly.

According to a further feature of the invention, therefore, we provide a process for the preparation of a diene of formula (II) whereby an ester of the compound of formula (I) is reacted, in the presence of a suitable base as described above with a reagent capable of replacing hydroxyl by a substituent X as defined above.

Thus, for example, an ester of the compound of formula (I) may be reacted in the presence of a tertiary organic base e.g. a tertiary amine as described above, for example, triethylamine with a sulphonylating agent such as a mesyl or tosyl halide in the presence or absence of halide ions, or with other acylating reagents serving to introduce a readily eliminatable group or with a halogenating reagent such as thionyl chloride. The conditions for such a reaction will in general be the conditions described above in relation to the preparation of the diene.

The esters of the compound of formula (I) may be prepared from the acid of formula (I) by reaction with an alcohol, phenol or stannanol or a reactive derivative thereof to form the desired ester. Reaction will desirably be effected under mild conditions in order to prevent rupture of the bicyclic nucleus. The use of neutral or mild acidic or basic conditions, therefore at temperatures between $-70°$ and $+35°$ C. is preferred.

The alkyl, alkoxyalkyl and aralkyl esters may be prepared by reaction of the acid of formula (I) with the appropriate diazoalkane or diazoaralkane e.g. diazomethane or diphenyldiazomethane. The reaction will generally be effected in an ether, ester or halohydrocarbon solvent, e.g. diethyl ether, ethyl acetate or dichloromethane. In general, reduced temperatures are preferred, for example $-15°$ to $+15°$ C.

The esters derived from alcohols may be produced by reaction of a reactive derivative of the alcohol having a readily displaceable substituent, for example, a halide such as the chloride, bromide or iodide, or a hydrocarbonsulphonyl derivative such as a mesyl or tosyl ester, with a salt of the acid of formula (I), e.g. an alkali or alkaline earth metal salt such as a lithium, sodium, potassium, calcium, or barium salt or an amine salt such as a triethylammonium salt. This reaction is preferably carried out in a substituted sulphoxide or amide solvent e.g. dimethyl sulphoxide, dimethylformamide or hexamethylphosphoramide.

Stannyl esters may conveniently be formed by reaction of the carboxylic acid of formula (I) or a salt thereof with reactive tetravalent tin moieties. Trialkyl tin oxides are preferred for the synthesis of tin compounds in view of their availability and low toxicity.

As indicated above, the dienes of formula (II) may be used as starting materials in the preparation of certain thio-analogues of the compounds of formula (I), namely compounds of the formula (IV)

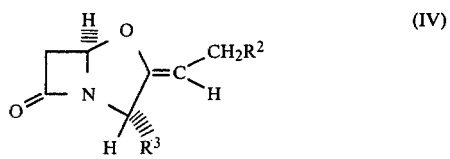
(IV)

(where $R^2$ is the residue of a sulphur nucleophile, and $R^3$ is a carboxyl or esterified carboxyl group) and salts of the compounds in which $R^3$ is a carboxyl group.

In general, $R^2$ may be represented by —SH, —SR$^4$ or —SO$_2$R$^4$ (where $R^4$ is an aliphatic, araliphatic, aromatic or heterocyclic group);

or by —SC=Y.R$^5$ (where Y is O or S and $R^5$ is a group as defined above for $R^4$ or a group OR$^4$ or SR$^4$, where $R^4$ is as defined above, or a group NR$^6$R$^7$, where $R^6$ and $R^7$, which may be the same or different, are hydrogen atoms or aliphatic, araliphatic or aromatic groups or together with the nitrogen atom to which they are attached represent a heterocyclic ring); or by SCN.

Thus, for example, when any one of the groups $R^4$, $R^5$, $R^6$ and $R^7$ is an aliphatic group, it may be an alkyl, alkenyl or alkynyl group, which may contain 1-6 carbon atoms or a cycloalkyl group, which may have 3-7, preferably 5 or 6, carbon atoms;

when any of the groups $R^4$, $R^5$, $R^6$ and $R^7$ is an araliphatic or aromatic group, it will desirably be an aralkyl group which may have 1-6 carbon atoms in the alkyl portion or an aryl group, the rings in such aryl and aralkyl groups preferably being monocyclic e.g. phenyl;

when either of the groups $R^4$ and $R^5$ is a heterocyclic group, it will desirably contain a carbon-attached 5-7 membered heterocyclic ring containing one or more heteroatoms such as nitrogen, sulphur or oxygen, and may carry one or more alkyl groups which may have 1-6 carbon atoms, e.g. a methyl group.

Such heterocyclic rings may be part of a bicyclic system and in this case may have heteroatoms in both rings. Where a nitrogen atom is present in the heterocyclic ring system, it may be in the form of the N-oxide. Examples of heterocyclic rings $R^4$ and $R^5$ include thiadiazolyl, diazolyl, triazolyl, tetrazolyl, thiazolyl, thiatriazolyl, oxazolyl, oxadiazolyl, benzimidazolyl, benzthiazolyl, benzoxazolyl, triazolopyridyl, purinyl, pyridyl or pyrimidyl rings.

Such groups identified above may themselves carry substituents such as hydroxyl or substituted hydroxyl, carboxyl or substituted carboxyl, amino or substituted amino groups or azido, mercapto, cyano or nitro groups. Heterocyclic rings carrying hydroxy, mercapto or amino substituents may exist in tautomeric forms. Where NR$^6$R$^7$ represents a heterocyclic ring, this may for example, contain 5-7 ring atoms, including one or more other hetero-atoms e.g. nitrogen, oxygen or sulphur atoms, and may be, for example, a piperidino, piperazino, morpholino or thiamorpholino ring, and may carry one or more alkyl groups which may have 1-6 carbon atoms, e.g. a methyl group.

Substituted hydroxy groups as referred to above include acylated and etherified hydroxy groups. In general, acylated hydroxy groups may have the formula $R^8CO_2$ where $R^8$ is an aliphatic, araliphatic or aromatic group while etherified hydroxy groups may have the formula $R^8O$, where $R^8$ has the above meaning. Substituted carboxyl groups may have the formula COOR$^8$, where $R^8$ has the above meaning, while substituted amino groups may have the formula NR$^6$R$^7$ as defined above, one of $R^6$ and $R^7$ being other than hydrogen. Preferred groups $R^6$, $R^7$ and $R^8$ are $C_{1-4}$ alkyl groups e.g. methyl.

The sulphur compounds in which $R^2$ represents —SH are preferred compounds for use as intermediates for the preparation of further sulphur compounds. The sulphur compounds of formula (IV) have been found to have a variety of uses. Thus, for example, they generally exhibit β-lactamase inhibitory activity and are of use in the protection of β-lactam antibiotics that are susceptible to β-lactamase hydrolysis. They have also demonstrated antibiotic activity against strains of gram-positive organisms, e.g. *Staphylococcus aureus*, aand against strains of gram-negative organisms e.g. *Haemophilus influenzae*. Furthermore, combinations of some thio-compounds with ampicillin have shown synergistic activity against β-lactamase producing strains of gram-positive organisms, e.g. *Staphylococcus aureus*, and some gram-negative organisms e.g. *Escherichia coli, Klebsiella aerogenes, Proteus mirabilis, Salmonella typhimurium, Shigella sonnei, Proteus morganii* and *Proteus vulgaris*.

According to a further feature of the invention we provide a process for the preparation of compounds of formula (IV) as defined above wherein a diene compound of formula (II) is reacted with a sulphur nucleophile in the presence of a substantially non-nucleophilic base or with a salt of the sulphur nucleophile and, where necessary a proton source, e.g. water, an alcohol or ammonium chloride, whereby a compound of formula (IV) is obtained, followed where an acid or salt of formula (IV) is required, by deesterification and, where required, by salt formation.

Suitable bases for use in the reaction with the sulphur nucleophile include tertiary amines which may carry aliphatic, araliphatic or aromatic groups, e.g. alkyl groups having up to 8 carbon atoms, aralkyl groups having up to 6 carbon atoms in the alkyl portion, or an aryl group, such aryl and aralkyl groups desirably being monocyclic. Amines bearing cycloaliphatic e.g. $C_{3-7}$ cycloalkyl groups or amines wherein the nitrogen atom forms part of a five-, six- or seven-membered heterocyclic ring optionally containing a further heteroatom e.g. N-alkyl piperidines or N-alkyl morpholines are also suitable.

Preferred organic bases include trialkylamines preferably having 1-6 carbon atoms in each alkyl group, especially methyl, ethyl, propyl or butyl groups, and trimethylamine and triethylamine are particularly suitable.

Other bases which may be used in the reaction with the sulphur nucleophile include alkali metal hydrides, alkoxides, dialkylamides, disilylamides, alkyls and aryls e.g. sodium, potassium or lithium hydrides or alkoxides or lithium dialkylamides, disilylamides, alkyls or aryls. In general, it is preferred to use as weak a base as possible which is effective in the reaction.

The above reaction will desirably be effected at or below ambient temperature, e.g. at from −80° C. to +20° C., preferably from −20° to +20° C. in solution in an inert solvent e.g. a halogenated hydrocarbon, such as dichloromethane; a substituted amide, such as dimethyl formamide; an ether such as tetrahydrofuran; or an ester such as ethyl acetate.

In one embodiment of the reaction, the sulphur nucleophile may be reacted with the diene and an inorganic base in a suitable aprotic liquid medium, e.g. a halogenated hydrocarbon solvent using a crown ether. A crown ether is a macrocyclic polyether, e.g. a number of ethyleneoxy units joined to form a ring, the internal diameter of the ring being approximately that of a particular metal ion. In general 6 ethyleneoxy units (18-crown-6) are suitable to entrain a potassium ion while 5 ethyleneoxy units (15-crown-5) are suitable for sodium. The ethyleneoxy units may carry substituents e.g. phenyl or cyclohexyl groups.

The inorganic base may, for example, be an alkali or alkaline earth metal hydroxide, carbonate or bicarbonate, e.g. potassium carbonate.

When one or more of the reactants, for example the base, is not soluble in the solvent in which the reaction takes place, a phase transfer reagent, for example a crown ether, may also be used to effect transfer of the reactant or reactants from the solid phase to the liquid phase or between two liquid phases.

A preferred single-liquid-phase system is dichloromethane with potassium carbonate/18-crown-6. Two preferred two-liquid-phase systems are water/dichloromethane with potassium hydroxide/dibenzo- or dicyclohexyl 18-crown-6 or potassium carbonate/18-crown-6.

It should be emphasised that in the presence of crown ethers or under phase transfer conditions the inorganic bases which are used are substantially non-nucleophilic in the sense used herein.

Where an ester of formula (IV) is prepared and a different ester or a carboxylic acid product is required the compound of formula (IV) prepared may be deesterified and, if desired, reesterified by methods described above. Where an acid of formula (IV) is to be prepared, it is preferred to employ a starting material, the ester group of which may subsequently readily be cleaved e.g. arylmethyl esters, for example benzyl, benzhydryl, trity 1, p-nitrobenzyl etc.

Cleavage of such an arylmethyl ester, e.g. a p-nitrobenzyl ester, may be effected by hydrogenolysis for example using a metal catalyst, e.g. a noble metal such as platinum, palladium or rhodium. The catalyst may be supported e.g. on charcoal or kieselguhr. A p-nitrobenzyl group may also be removed by reduction of the nitro group (e.g. using a dissolving metal reducing agent such as zinc in acetic acid, or zinc in aqueous tetrahydrofuran or acetone controlled, for example, in the pH range 3–6, preferably 4.0–5.5 by the addition of aqueous hydrochloric acid; aluminium amalgam in a moist ether, e.g. tetrahydrofuran; or iron and ammonium chloride in an aqueous ether e.g. tetrahydrofuran) followed by hydrolysis either under reduction conditions or by subsequent treatment with acid. Alternatively, a stannyl ester can be cleaved by very mild solvolysis, e.g. by reaction with water, alcohols, phenols or carboxylic acids, e.g. acetic acid.

Where a salt of an acid of formula (IV) is required, the acid may be reacted with a suitable base, solvents and reaction conditions preferably being chosen to favour precipitation of the desired salt. Thus, for example, in the formation of alkali metal salts, e.g. sodium salts, it is preferred to add to a solution of the acid in a solvent such as ethyl acetate, an alkali metal alkanoate, e.g. a 2-ethylhexanoate.

The resulting thio-compound may be isolated and purified by conventional techniques.

The following Preparation and Examples are given by way of illustration only; all temperatures are in °C. Melting points were determined in capilliary tubes with a Mettler FP5 melting point apparatus.

PREPARATION 1

4-Nitrobenzyl(3R,5R,Z)-2-(2-chloroethylidine)-clavam-3-carboxylate

A solution of 4-nitrobenzyl (3R,5R,Z)-2-(2-hydroxyethylidene)-clavam-3-carboxylate (1.0 g) in ethyl acetate (20 ml) containing pyridine (0.32 ml) was cooled to −60°, stirred and treated with a solution of thionyl chloride (0.26 ml) in ether (2.0 ml). The mixture was warmed to −10° and stirred for a further 10 min. at −10° to 0° and then diluted with ether (250 ml). The mixture was washed successively with 0.5 N aqueous hydrochloric acid, water, saturated aqueous sodium hydrogen carbonate solution (until the washings were colourless) and water. The ether layer was dried and concentrated to give a slurry of colourless needles which were collected by filtration washed with ether and dried to give the chloro ester (320 mg.), $[\alpha]_D + 30°$ (c 0.49, DMSO) $\lambda_{max}^{EtOH}$ 264 nm ($\epsilon$10,550), $\nu_{max}$ (CHBr$_3$) 1800 ($\beta$-lactam), 1753 (ester) 1692 cm$^{-1}$ (O—C=C), $\tau$(CDCl$_3$) values include 4.25 (d, J2C-5H), 4.7 (s, benzylic protons), 5.08 (t, J8 Hz, =CH—), 5.82 (d. J 8 Hz, CH$_2$Cl).

EXAMPLE 1

4-Nitrobenzyl (5R)-2-vinylclav-2-em-3-carboxylate

To a stirred solution of triethylamine (0.135 ml.) in tetrahydrofuran (10 ml.) at 0° was added 4-nitrobenzyl (3R,5R,Z)-2-(2-chloroethylidene)clavam-3-carboxylate (0.352 g.). The mixture was maintained at 0° and stirred for 45 minutes and was then partitioned between an ice cold mixture of water (250 ml.), 0.5 N aqueous hydrochloric acid (10 ml.) and ether (250 ml.). The organic layer was washed with ice cold water, dried over magnesium sulphate and concentrated to give a slurry of crystals. The crystals were collected and dried to afford the title ester (0.1 g.), $[\alpha]_D + 9°$ (c 1.0, DMSO), $\nu_{max}$(CHBr$_3$) 1810($\beta$-lactam), 1710(ester), 1638(enol ether), 1528 and 1350 cm$^{-1}$(NO$_2$), $\tau$(CDCl$_3$) 1.76 and 2.36(aromatic protons),2.94(dd, J10 and 17 Hz, —CH=CH$_2$), 4.01(dd, J 2 and 3 Hz, C-5 H), 4.03(dd, J 2 and 17 Hz, olefinic proton), 4.32(dd, J 2 and 10 Hz, olefinic proton), 4.60(ABq, J 14 Hz, CH$_2$Ar), 6.13 and 6.47(dd, J 3 and 17 Hz, and dd, J 2 and 17 Hz, C-6 protons).

EXAMPLE 2

4-Nitrobenzyl (5R)-2-vinylclav-2-em-3-carboxylate

Solutions of triethylamine (1.05 ml) in dichloromethane (5 ml) and mesyl chloride (0.425 ml) in dichloromethane (5 ml) were added dropwise and concurrently to a stirred solution of 4-nitrobenzyl (3R,5R,Z)-2-(2-hydroxyethylidene) clavam-3-carboxylate (1.67 g) in dichloromethane (25 ml) at 0° over a period of ca 1 minute. The mixture was stirred for a further 30 seconds and partitioned between ether and ice cold water. The organic phase was washed successively with 0.5 N hydrochloric acid, saturated aqueous sodium hydrogen carbonate and saturated brine. The solution was dried over magnesium sulphate, concentrated to ca 20 ml and poured into a vigorously stirred mixture of ether (60 ml) and petroleum spirit (80 ml). Some precipitated material was removed by filtration and the filtrate crystallised on standing. The crystals were collected and dried to give the title ester (0.30 g), $[\alpha]_D + 8.5°$ (c 1.0, DMSO). The spectroscopic characteristics of the product were similar to those described in Example 1.

EXAMPLE 3

4-Nitrobenzyl (5R)-2-vinylclav-2-em-3-carboxylate

A solution of 4-nitrobenzyl (3R,5R,Z)-2-(2-hydroxyethylidene)-clavam-3-carboxylate (2.0 g) in tetrahydrofuran (30 ml) and pyridine (2.78 ml) was cooled to −65°, stirred, and treated with thionyl chloride (0.52 ml). After a temperature rise of ca. 30°, the mixture was cooled to −65°, allowed to warm to 0°, and maintained at 0° for 10 min. Triethylamine (3.0 ml) was then added, and after stirring for 15 minutes at 0°, the resulting suspension was poured with stirring into a chilled (10°) mixture of concentrated hydrochloric acid (16 ml), water (300 ml) and ether (400 ml). The ether layer was washed with water (5×400 ml), dried, charcoaled, filtered through Kieselguhr, and evaporated to leave a pale yellow crystalline solid (0.628 g). A solution of the crude product in dichloromethane (10 ml) was treated with charcoal, filtered through Kieselguhr, and evaporated to leave a slurry of crystals. The solid was collected by filtration, washed with ether, and dried in vacuo to afford the title ester (0.49 g), $[\alpha]_D + 11°$ (c, 1.03, CHCl$_3$). N.m.r. and i.r. spectra resembled those of Example 1.

EXAMPLE 4

Methyl (5R)-2-vinylclav-2-em-3-carboxylate

A solution of thionyl chloride (0.27 ml) in dry tetrahydrofuran (2 ml) was added dropwise, under nitrogen, to a stirred solution of methyl (3R,5R,Z)-2-(2-hydroxyethylidene) clavam-3-carboxylate (0.64 g) in dry tetrahydrofuran (15 ml) containing dry pyridine (0.40 ml) at −20°. The resulting mixture was allowed to warm to 0° over a period of 5 minutes and after a further 15 minutes the mixture was poured into ether (200 ml) and water (50 ml). The organic phase was washed successively with water (50 ml), pH 7 buffer (2×40 ml), and water (40 ml) and then dried over magnesium sulphate. The filtered organic solution contained 0.29 g of material and was concentrated to ca. 40 ml, then cooled to 0°, and treated with a solution of triethylamine (0.17 ml) in ether (1 ml). After 15 minutes the mixture was partitioned between ether (100 ml) and water (40 ml). The organic phase was washed with water (40 ml), then dried over magnesium sulphate, and filtered to give an ethereal solution of the title ester (0.10 g) which was stored at 0°; a portion of this solution was evaporated to afford the title ester as an oil. $\nu_{max}$ (CHBr$_3$) 1802 (β-lactam), 1708 (CO$_2$R), 1632 and 1568 cm$^{-1}$ (C=C), $\tau$ (CDCl$_3$) 2.96 (dd, J 11 and 17 Hz, C$\underline{H}$=CH$_2$), 4.09 (dd, J 2 and 3 Hz, C-5 H), 4.10 (dd, J 2 and 17 Hz, olefinic proton), 4.38 (dd, J 2 and 11 Hz, olefinic proton), 6.17 (s, OCH$_3$), 6.21 and 6.50 (dd, J 3 and 17 Hz, and dd, J 2 and 17 Hz, C-6 protons).

EXAMPLE 5

Benzyl (5R)-2-vinylclav-2-em-3-carboxylate

A solution of thionyl chloride (0.18 ml) in ether (1.2 ml) was added dropwise, under nitrogen, to a stirred solution of benzyl (3R,5R,Z)-2-(2-hydroxyethylidene)-clavam-3-carboxylate (0.58 g) in ethyl acetate (9 ml), ether (3 ml), and dry tetrahydrofuran (1.2 ml) containing dry pyridine (0.27 ml), at −20°. The resulting mixture was allowed to warm to 0° over a period of 5 minutes and after a further 15 minutes the mixture was poured into ether (115 ml) and water (35 ml). The organic phase was washed successively with water (2×35 ml), pH7 buffer (2×40 ml), and water (35 ml) and then dried over magnesium sulphate. The filtered organic solution contained ca. 0.40 g of material and was concentrated to 73 ml. A portion of this solution (36 ml) was cooled to 0° and treated with a solution of triethylamine (0.09 ml) in ether (1 ml) with stirring. After 25 minutes the mixture was partitioned between ether (60 ml) and water (45 ml). The organic phase was washed with water (45 ml), followed by saturated brine (30 ml), then dried over magnesium sulphate and filtered to afford an ethereal solution of the title ester (0.120 g) which was stored at 0°; a portion of this solution was evaporated to afford the title ester as an oil. $\nu_{max}$ (CHBr$_3$) 1804 (β-lactam), 1702 (CO$_2$R), 1632 cm$^{-1}$ (enol ether), $\tau$ (CDCl$_3$) 2.5 to 2.7 (m, aromatic protons), 2.91 (dd, J 11 and 17 Hz, C$\underline{H}$=CH$_2$), 4.05 (dd, J 2 and 3 Hz, C-5 H), 4.07 (dd, J 2 and 17 Hz, olefinic proton), 4.36 (dd, J 2 and 11 Hz, olefinic proton), 4.68 (s, benzylic proton), 6.19 and 6.50 ) dd, J 3 and 17 Hz, and dd, J 2 and 17 Hz, C-6 protons).

EXAMPLE 6

4-Nitrobenzyl (3R,5R,Z)-2-(2-acetylthioethylidene)clavam-3-carboxylate

A stirred solution of 4-nitrobenzyl (5R)-2-vinylclav-2-em-3-carboxylate [1.375 g, $[\alpha]_D + 7°$ (c 1.0, DMSO)] and thioacetic acid (0.34 ml.) in dichloromethane (20 ml.) at 0° was treated with a solution of triethylamine in dichloromethane (0.1 M, 43.5 ml.) at 0°. After 8 minutes the mixture was diluted with ether (500 ml.) and washed with 0.5 N aqueous hydrochloric acid (30 ml.) followed by brine. The organic solution was dried over sodium sulphate and evaporated to an oil (1.67 g) which crystallised on trituration with ethyl acetate. The crystals were collected and dried to afford the title ester (0.435 g.), m.p. 90.2° (Mettler), $[\alpha]_D + 9°$ (c 1.0, DMSO), $\lambda_{max}$ (EtOH) 238 and 262.5 nm ($\epsilon$12,500 and 12,000), $\nu_{max}$ (Nujol) 1806 (β-lactam), 1744 (CO$_2$R), 1682 (RCOS and enol ether), 1520 and 1348 cm$^{-1}$ (NO$_2$), $\tau$ (CDCl$_3$) 1.77 and 2.49 (doublets, J 8 Hz, aromatic proton), 4.28 (d, J 2 Hz, C-5 H), 4.71 (ABq, J 14 Hz, C$\underline{H}_2$Ar), 4.91 (s, C-3 H), 5.23 (t, J 8 Hz, =CH—), 6.43 (d, J 8 Hz, C$\underline{H}_2$SCOCH$_3$), 6.48 and 6.90 (dd, J 2 and 17 Hz, and d, J 17 Hz, C-6 protons), 7.68 (s, SCOCH$_3$).

EXAMPLE 7

4-Nitrobenzyl (3R,5R,Z)-2-(2-N,N-dimethylthiocarbamoylthioethylidene)clavam-3-carboxylate A stirred suspension of 4-nitrobenzyl (5R)-2-vinylclav-2-em-3-carboxylate [1.18 g $[\alpha]_D + 6°$ (c 1.0, DMSO)] and sodium dimethyldithiocarbamate (0.572 g)

in dichloromethane (60 ml) at 20° was treated successively with glacial acetic acid (0.29 ml) and a solution of triethylamine in dichloromethane (0.1 M 37.2 ml). After 15 minutes the mixture was diluted with ether (500 ml) and washed with 0.5 N aqueous hydrochloric acid followed by brine. The organic solution was dried over sodium sulphate and evaporated to an oil (1.20 g) which was chromatographed on a column of silica gel eluting with ether-petroleum ether (b.p. 60°-80°) (1:1). Appropriate fractions were combined on the basis of thin layer chromatography and evaporated to leave an oil (0.415 g) which crystallised on trituration with ether. The crystals were collected and dried in vacuo to afford the title ester (0.230 g), m.p. 92.3° (Mettler), $[\alpha]_D -6.7°$ (c 1.2, DMSO), $\lambda_{max}$ (EtOH) 273.5 nm ($\epsilon$18,300), $\nu_{max}$ (Nujol) 1795 ($\beta$-lactam), 1746 ($CO_2R$), 1686 (O—C=C), 1520 and 1348 cm$^{-1}$ ($NO_2$), $\tau$(CDCl$_3$) 1.77 and 2.48 (doublets, J 9 Hz, aromatic protons), 4.27 (d, J 3 Hz, C-5 H), 4.60 and 4.80 (AB quartet, J 13 Hz, benzylic protons), 4.87 (s, C-3 H), 4.98 (t, J 8 Hz, =CH—), 5.99 (d, J 8 Hz, $CH_2S$), 6.44 and 6.64 (broad singlets, $NMe_2$), 6.48 and 6.90 (dd, J 3 and 17 Hz; and d, J 17 Hz, C-6 protons).

EXAMPLE 8

4-Nitrobenzyl(3R,5R,Z)-2-(2-phenylthioethylidene)-clavam-3-carboxylate

A stirred solution of 4-nitrobenzyl (5R)-2-vinylclav-2-em-3-carboxylate [0.474 g, $[\alpha]_D+7°$ (c 1.0, DMSO)] and thiophenol (0.17 ml) in dichloromethane (20 ml) at 0° was treated with a solution of triethylamine in dichloromethane (0.1 M, 15.0 ml) at 0°. After 1 minute the mixture was added to a stirred mixture of ether (250 ml) and 0.5 N aqueous hydrochloric acid (20 ml). The organic phase was washed with brine and then dried over sodium sulphate. Evaporation of the organic solution gave an oil (0.500 g) which was chromatographed on a column of silica gel eluting with ether-petroleum ether (b.p. 40°-60°) (1:1). Appropriate fractions were combined and evaporated to afford the title ester (0.200 g), $[\alpha]_D+9°$ (c 1.0, DMSO), $\lambda_{max}$ (EtOH) 259 nm ($\epsilon$10,800). $\nu_{max}$(CHBr$_3$) 1796 ($\beta$-lactam), 1748 ($CO_2R$), 1690 (O—C=C), 1524 and 1346 cm$^{-1}$ ($NO_2$), $\tau$ (CDCl$_3$) 1.70 and 2.44 (doublets, J 9 Hz, aromatic protons), 2.60 (s, S—Ph), 4.33 (d, J 3 Hz, C-5 H), 4.71 (s, benzylic protons), 4.83 (s, C-5 H), 5.15 (t, J 8 Hz, =CH—), 6.33 (d, J 8 Hz, —$CH_2$—S), 6.50 and 7.03 (dd, J 3 and 17 Hz; and d, J 17 Hz, C-6 protons).

EXAMPLE 9

4-Nitrobenzyl (3R,5R,Z)-2-[2-(pyrid-2-ylthio)ethylidene] clavam-3-carboxylate

A stirred solution of 4-nitrobenzyl (5R)-2-vinylclav-2-em-3-carboxylate (0.47 g) and 2-mercaptopyridine (0.176 g) in dichloromethane (37.5 ml) was treated with triethylamine (0.22 ml). After 2 minutes the mixture was diluted with ether (300 ml) and washed with 0.5 N aqueous hydrochloric acid (30 ml) followed by brine. The organic solution was dried over sodium sulphate and evaporated to leave an oil which was chromatographed on a column of silica gel eluting with ether-petroleum ether (b.p. 40°-60°) (1:4). Appropriate fractions were combined on the basis of thin layer chromatography and evaporated to afford the title ester (0.070 g), $\nu_{max}$ (CHBr$_3$) 1792 ($\beta$-lactam), 1748 ($CO_2R$), 1690 (O—C=C), 1522 and 1343 cm$^{-1}$ ($NO_2$), $\tau$ (CDCl$_3$) 1.63 (d, J 5 Hz, pyridyl C-6 H), 2.44 (dd, J 7 and 8 Hz, pyridyl C-4 H), 2.85 (d, J 6 Hz pyridyl C-3 H), 3.03 (dd, J 5 and 7 Hz, pyridyl C-5 H), 1.87 and 2.57 (doublets, J 9 Hz, aromatic protons), 4.29 (d, J 3 Hz, C-5 H), 4.69 and 4.85 (AB quartet, J 18 Hz, benzylic protons), 4.91 (s, C-3 H), 6.06 (t, J 9 Hz, =CH—), 6.12 (d, J 8 Hz, $CH_2$—S), 6.48 and 6.91 (dd, J 3 and 17 Hz; and d, J 17 Hz, C-6 protons).

EXAMPLE 10

4-Nitrobenzyl (3R,5R,Z)-2-(2-methylthioethylidene)clavam-3-carboxylate

A solution of diisopropylamine (0.242 g) in tetrahydrofuran (28 ml) was treated with a 22% n-butyllithium solution in hexane (0.67 ml) at −20° under nitrogen. After 5 minutes the mixture was provided with a solution of methanethiol in tetrahydrofuran (20% w/v, 1.06 ml) and after a further 5 minutes a solution of 4-nitrobenzyl (5R)-2-vinylclav-2-em-3-carboxylate [0.632 g, $[\alpha]_D+8.5°$ (c 1.0, DMSO)] in tetrahydrofuran (28 ml) was added in one portion. After 90 seconds the mixture was diluted with ether (400 ml) and washed with 0.5 N aqueous hydrochloric acid followed by brine. The organic solution was dried over magnesium sulphate and evaporated to an oil (0.793 g) which was chromatographed on a column of silica gel eluting with ether-petroleum ether (b.p. 40°-60°) (2:1). Appropriate fractions were combined and evaporated to afford the title ester (0.083 g) $[\alpha]+9°$ (c 1.2, DMSO), $\lambda_{max}$ (EtOH) 263.5 nm ($\epsilon$10,500), $\nu_{max}$(CHBr$_3$) 1798 ($\beta$-lactam), 1752 ($CO_2R$), 1690 (O—C=C), 1522 and 1348 cm$^{-1}$ ($NO_2$), $\tau$ (CDCl$_3$) 1.88 and 2.50 (doublets, J 9 Hz, aromatic protons), 4.33 (d, J 3 Hz, C-5 H), 4.72 (s, benzylic protons), 4.88 (s, C-3 H), 5.28 (t, J 8 Hz, =CH—), 6.50 and 6.96 (dd, J 3 and 17 Hz; and d, J 17 Hz, C-6 protons) 6.83 (d, J 8 Hz, —$CH_2$—S), 8.05 (s, S—Me).

EXAMPLE 11

4-Nitrobenzyl (3R,5R,Z) 2-(2-methylthioethylidene)clavam-3-carboxylate

A solution of methanethiol in tetrahydrofuran (20% w/v, 0.32 ml) was diluted with tetrahydrofuran (10 ml) and then treated with a 22% n-butyllithium solution in hexane (0.2 ml) at −20° under nitrogen. After 5 minutes the mixture was provided with a solution of 4-nitrobenzyl (5R)-2-vinylclav-2-em-3-carboxylate [0.190 g, $[\alpha]_D+8.5°$ (c 1.0, DMSO)] in tetrahydrofuran (10 ml). After 45 seconds the mixture was diluted with ether (300 ml) and washed with 0.5 N aqueous hydrochloric acid followed by brine. The organic solution was dried over magnesium sulphate and evaporated to an oil (0.220 g) which was chromatographed on a column of silica gel eluting with ethyl acetate-petroleum ether (b.p. 40°-60°) (1:1). Appropriate fractions were combined and evaporated to afford the title ester (0.046 g) whose physical and spectroscopic properties resembled those described in Example 10.

EXAMPLE 12

4-Nitrobenzyl (3R,5R,Z)-2-(2-ethylthioethylidene)clavam-3-carboxylate

A solution of diisopropylamine (0.360 g) in tetrahydrofuran (30 ml) was treated with a 22% n-butyllithium solution in hexane (1.0 ml) at −20° under nitrogen. After 10 minutes the mixture was provided with a solution of ethanethiol in tetrahydrofuran (1% w/v, 22.3 ml) and after a further 5 minutes a solution of 4-nitrobenzyl (5R)-2-vinylclav-2-em-3-carboxylate [0.950 g, $[\alpha]_D + 9°$ (c 1.0, DMSO)] in tetrahydrofuran (20 ml) was added in one portion. After 3 minutes the mixture was diluted with ether (500 ml) and washed with 0.5 N aqueous hydrochloric acid (50 ml) followed by brine. The organic solution was dried over sodium sulphate and evaporated to an oil (1.10 g) which was chromatographed on a column of silica gel eluting with ether. Fractions were combined on the basis of thin layer chromatography and evaporated to afford the title ester (0.06 g), $\nu_{max}$ (CHBr$_3$) 1798 ($\beta$-lactam), 1750 (CO$_2$R), 1692 (O—C=C), 1522 and 1346 cm$^{-1}$ (NO$_2$), $\tau$ (CDCl$_3$) 1.80 and 2.48 (doublets, J 9 Hz, aromatic protons), 4.33 (d, J 3 Hz, C-5 H), 4.72 (s, benzylic protons), 4.88 (s, C-3 H), 5.29 (t, J 8 Hz, =CH—), 6.48 and 6.98 (dd, J 3 and 17 Hz; and d, J 17 Hz, C-6 protons), 6.77 (d, J 8 Hz, —CH$_2$—S), 7.59 (q, J 7 Hz, SCH$_2$CH$_3$), 8.81 (t, J 7 Hz, SCH$_2$CH$_3$).

EXAMPLE 13

4-Nitrobenzyl (3R,5R,Z,)-2-(2-mercaptoethylidene)clavam-3-carboxylate

A solution of 4-nitrobenzyl (5R)-2-vinylclav-2-em-3-carboxylate (100 mg) and 18-Crown-6 (40 mg) in dichloromethane (5 ml) was saturated with hydrogen sulphide at 20°, stirred, and treated with anhydrous potassium carbonate (20 mg). After stirring and passing hydrogen sulphide for 17 minutes, the mixture was diluted with ethyl acetate (50 ml) and washed with 0.5 N hydrochloric acid (20 ml) and water (3×20 ml). The organic layer was then dried and evaporated under reduced pressure. The residue was crystallised from ethyl acetate-ether to afford the title ester as needles (81 mg), m.p. 128.7° (M), $[\alpha]_D + 20°$ (c 1.02, DMSO), $\lambda_{max}^{EtOH}$ 262.5 nm ($\epsilon$11,500), $\nu_{max}$ (Nujol) 2580 (SH), 1790 ($\beta$-lactam), 1745 (ester), 1686 (O—C=C), 1514 and 1342 cm$^{-1}$ (NO$_2$), $\tau$ (CDCl$_3$) values include 4.22 (d, J 2 Hz, C-5 H), 4.84 (s, C-3 H), 5.12 (t, J 7 Hz, =CH—), 6.44 (dd, J 17 and 2 Hz, C-6 $\alpha$ H), and 8.40 (t, J 8 Hz, —SH).

EXAMPLE 14

4-Nitrobenzyl (3R,5R,Z)-2-(2-ethylthioethylidene)clavam-3-carboxylate

A solution of 4-nitrobenzyl (5R)-2-vinylclav-2-em-3-carboxylate (200 mg), ethanethiol (112 mg) and 18-Crown-6 (80 mg) in dichloromethane (10 ml) was stirred with anhydrous potassium carbonate (41 mg) at room temperature for 11 minutes. The mixture was then diluted with ethyl acetate (100 ml) and washed with 0.5 N hydrochloric acid (50 ml) and water (3×50 ml). The organic layer was dried and evaporated to leave a gum which was chromatographed on a column of silica gel, eluting with ether, to afford the title ester as a gum (166 mg), $\nu_{max}$ (CHBr$_3$) 1794 ($\beta$-lactam), 1750 (ester), 1690 (O—C=C), 1528 and 1348 cm$^{-1}$ (NO$_2$), $\tau$ (CDCl$_3$) values include 4.32 (d, J 2 Hz, C-5 H), 4.88 (s, C-3 H), 5.26 (t, J 8 Hz, —CH=), 6.48 (dd, J 17 and 2 Hz, C-6 $\alpha$ H), and 8.79 (t, J 7 Hz, —CH$_3$).

EXAMPLE 15

4-Nitrobenzyl (3R,5R,Z)-2-[2-(2-hydroxyethylthio)ethylidene]-clavam-3-carboxylate 4-Nitrobenzyl (5R)-2-vinylclav-2-em-3-carboxylate (300 mg) was reacted with 2-mercaptoethanol (150 mg) for 14 minutes as in Example 14 to afford, after a similar work-up and chromatography, the title ester as a gum (225 mg), $[\alpha]_D + 20°$ (c, 1.41, DMSO), $\lambda_{max}^{EtOH}$ 262 nm ($\epsilon$, 10,500), $\nu_{max}$ (CHBr$_3$) 3602 (OH), 1800 ($\beta$-lactam), 1754 (ester), 1692 (O—C=C), 1526 and 1348 cm$^{-1}$ (NO$_2$), $\tau$ (CDCl$_3$) values include 4.30 (d, J 3 Hz, C-5 H), 5.26 (t, J 8 Hz, =CH—), 6.31 (t, J 7 Hz, —CH$_2$OH), 6.48 (dd, J 17 and 3 Hz, C-6 $\alpha$ H), and 7.39 (t, J 7 Hz, S-CH$_2$CH$_2$OH).

EXAMPLE 16

4-Nitrobenzyl (3R,5R,Z)-2-[2-(prop-1-en-3-ylthio)ethylidene]-clavam-3-carboxylate 4-Nitrobenzyl (5R)-2-vinylclav-2-em-3-carboxylate (1.50 g) was reacted with allylmercaptan (1.13 ml) for 26 minutes as in Example 14 and worked up similarly to afford the title ester (2.17 g), $\lambda_{max}^{EtOH}$ 263.5 nm ($\epsilon$9,650), $\nu_{max}$ (CHBr$_3$) 1798 ($\beta$-lactam), 1752 (ester), 1690 (O—C=C), 1521 and 1346 cm$^{-1}$ (NO$_2$), $\tau$ (CDCl$_3$) values include 4.30 (d, J 3 Hz, C-5 H), 5.25 (t, J 8 Hz, =CH—), and 6.46 (dd, J 17 and 3 Hz, C-6 $\alpha$ H).

EXAMPLE 17

4-Nitrobenzyl (3R,5R,Z)-2-(2-phenylsulphonylethylidene) clavam-3-carboxylate 4-Nitrobenzyl (5R)-2-vinylclav-2-em-3-carboxylate (316 mg) was reacted with benzenesulphinic acid (200 mg) for 2.5 minutes as in Example 14 and worked up similarly to afford, after chromatography, the title ester (77 mg), m.p. 163.8 (Mettler), $[\alpha]_D + 34.5°$ (c 1.015, DMSO), $\lambda_{max}^{EtOH}$ 265, 271.5 nm ($\epsilon$, 13,400, 13,300), $\nu_{max}$ (CHBr$_3$) 1796 ($\beta$-lactam), 1750 (ester), 1690 (O—C=C), 1526 and 1348 cm$^{-1}$ (NO$_2$), $\tau$ (CDCl$_3$) values include 4.64 (d, J 2 Hz, C-5 H), 4.72 (s, benzylic protons), 5.20 (t, 7 Hz, =CH—), and 6.12 (d, J 7 Hz, —CH$_2$—SO$_2$—).

EXAMPLE 18

Benzyl (3R,5R,Z)-2-[2-(2-hydroxyethylthio)ethylidene]-clavam-3-carboxylate

Benzyl (5R)-2-vinylclav-2-em-3-carboxylate (190 mg), prepared as in Example 5 was reacted with 2-mercapto ethanol (112 mg) for 9 minutes as in Example 14 to afford after a similar work-up and chromatography, the title ester as a gum (43 mg), $[\alpha]_D + 12°$ (c 1.07, CHCl$_3$), $\nu_{max}$ (CHBr$_3$) 3590 (OH), 1794 ($\beta$-lactam), 1746 (ester), 1690 (O—C=C) and 750 (—Ph), $\tau$ (CDCl$_3$) values include 2.68 (aromatic protons), 4.38 (d, J 3 Hz, C-5 H), 6.38 (t, J 7 Hz, —CH$_2$OH), 6.53 (dd, J 16 and 3 Hz, C-6 $\alpha$ H), 6.80 (d, J 8 Hz, =CH$_2$-S), and 7.47 (t, J 7 Hz, S—CH$_2$—CH$_2$OH).

We claim:
1. Crystalline 4-nitrobenzyl (5R)-2-vinylclav-2-em-3-carboxylate.

* * * * *